United States Patent [19]
Roggero et al.

[11] Patent Number: 6,075,127
[45] Date of Patent: Jun. 13, 2000

[54] PREPARATION OF PURIFIED (POLY)PEPTIDES

[75] Inventors: Mario Roggero, Servion; Giampietro Corradin, Lausanne; Christophe Reymond, Prilly; Nicolas Fasel, Epalinges, all of Switzerland

[73] Assignee: RMF Dictagene SA, Switzerland

[21] Appl. No.: 09/254,567

[22] PCT Filed: Sep. 9, 1997

[86] PCT No.: PCT/EP97/04939

§ 371 Date: May 26, 1999

§ 102(e) Date: May 26, 1999

[87] PCT Pub. No.: WO98/09983

PCT Pub. Date: Mar. 12, 1998

[30] Foreign Application Priority Data

Sep. 9, 1996 [EP] European Pat. Off. .............. 96202515
May 2, 1997 [EP] European Pat. Off. .............. 97201318

[51] Int. Cl.$^7$ ................................. A23J 1/00; C07K 1/00
[52] U.S. Cl. ......................... 530/412; 435/69.1; 435/333; 435/334; 435/335; 435/344; 530/402; 530/413; 530/417
[58] Field of Search ..................................... 435/69.1, 333, 435/334, 335, 344; 530/402, 412, 413, 417

[56] References Cited

PUBLICATIONS

Hochuli et al. Genetic Appropach to Facilitate Purification of Recombinant Proteins with a Novel Metal Chelate Adsorbent. Bio/Technology 6(11): 1321–1325, 1988.

Sassenfeld, Helmut, M. Engineering Proteins for Purification. Trends in Biotechnology. 8(4) 88–93, 1990.

Krieger et al. Affinity Purification of Synthetic Peptides. Proc. Natl. Acad. Sci. 73(9): 3160–3164, 1976.

*Primary Examiner*—Karen Cochrane Carlson
*Assistant Examiner*—Holly Schnizer

[57] ABSTRACT

The invention provides for a method for the modification of (poly)peptides for facilitating purification thereof, which modification method comprises the insertion of at least one specifically cleavable amino acid at the end of the (poly)peptide chain during synthesis thereof and protecting the same amino acid(s) within the (poly)peptide, if present, against cleavage, in order to allow for specific cleavage precisely at the specifically cleavable amino acid(s). The invention further relates to a process for the preparation of purified (poly)peptides using the modification method. The process comprises the steps of synthesizing the desired (poly)peptide; adding at least one specifically cleavable amino acid at the end of the (poly)peptide, while having protected the same amino acid(s) within the (poly)peptide, if present, against cleavage; elongating the (poly)peptide and the amino acid(s) added thereto with a tag sequence to obtain an elongated (poly)peptide; purifying the elongated (poly) peptide by means of a tag-specific purification method; and removing the tag sequence and the additional amino acid(s) from the elongated (poly)peptide by means of a cleavage method specific for the additional amino acid(s) to obtain the purified (poly)peptide.

8 Claims, 5 Drawing Sheets

FIG.1  Mass spectrum of crude peptide

FIG. 2  Chromatographic profile of IMAC purification.

FIG.3. Mass spectrum of purified peptide

FIG. 4 Chromatographic profile of crude (A) peptide

FIG. 4 Chromatographic profile of purified (B) peptide

```
                        SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: His tag sequence

<400> SEQUENCE: 1

His His His His His His Gly Gly Met
1               5
```

PREPARATION OF PURIFIED (POLY) PEPTIDES

This is a U.S. National Stage Application of PCT/EP97/04939 filed Sep. 9, 1997.

BACKGROUND OF THE INVENTION

1. Field of the Invention

The present invention relates to a modification method for facilitating the preparation of purified (poly)peptides and to a purification process using this modification method.

2. Description of the Related Art

During the last years solid phase peptide synthesis, using either t-Boc or F-moc strategies, has been largely improved. Sophisticated protocols of synthesis allowed the preparation of polypeptides of about 100 residues or more[1-4]. Nevertheless, incomplete coupling and chain termination that may occur at any cycle of the peptide assembly leads to the formation of deletion—and truncated sequences.

This and the possible occurrence of side reactions observed mainly during the final cleavage from the resin hamper the straightforward isolation of the desired peptide from other impurities. The purification of long synthetic polypeptides is a major problem in the production of products useful for biological studies and for human and animal use where a high level of purity is mandatory.

In particular, when sequences containing 30 or more residues are synthesized, the differences in physical properties such as size, charge and hydrophobicity between the desired product and deleted, truncated or modified peptide impurities may be too small to allow adequate purification. In addition, the modern powerful separation techniques, i.e. reverse phase HPLC, are often limited by low yields and small sample loadability which is time-consuming and expensive. Different approaches have been already tested to circumvent this limitation. Biotinylation of a 153 residue IL-1 synthetic protein[5] and of a 99 residue SIV protease synthetic protein[6] were performed and the biotinylated chains were isolated on an avidin-agarose column.

Ball et al.[7] have recently proposed a purification procedure based on the addition of a reversible protecting group which bears either lipophilic, acidic or basic functions to the last residue of the peptide chain.

More specific chromatographic methods have been optimized exploiting the presence of particular residues in the synthesized sequences. For example, cysteine-containing peptides have been purified by reaction with immobilized mercury derivatives[8] or activated thiols[9] and immobilized metal ion affinity chromatography (IMAC)[10] has been successfully applied for the purification of peptides containing histidine or tryptophan[11].

In recombinant proteins a histidine tail, B cell epitope or GST moieties were purposely added. These tails could subsequently be used in affinity chromatography.

In general, a purification protocol which is based on the physico-chemical properties of the synthesized peptide has to be optimized for each individual sample, which is a time-consuming and costly exercise. For these reasons, a number of techniques have been developed to render purification procedures of general applicability[15]. However, the methods described so far are not completely satisfactory since they are still time consuming and/or leave covalently derivatized peptides in the final purified products which may pose some concern for their biological and physico-chemical properties and their final utilization in animals and humans.

It is therefore the object of the present invention to provide an improvement to the known methods by providing a method for the modification of (poly)peptides for facilitating purification thereof, and to a purification process for (poly)peptides, which method and process are universally applicable, result in a high yield of recovery and are easy to perform.

This object was achieved according to the invention by a modification method, which comprises the insertion of at least one specifically cleavable amino acid at the end of the (poly)peptide chain during synthesis thereof and protecting the same amino acid(s) within the (poly)peptide, if present, against cleavage, in order to allow for specific cleavage precisely at the specifically cleavable amino acid(s).

SUMMARY OF THE INVENTION

A purification process using this modification method, comprises the steps of:
 a) synthesizing the desired (poly)peptide;
 b) adding at least one specifically cleavable amino acid at the end of the (poly)peptide, while having protected the same amino acid(s) within the (poly)-peptide, if present, against cleavage;
 b) elongating the (poly)peptide and the amino acid(s) added thereto with a tag sequence to obtain an elongated polypeptide;
 c) purifying the elongated polypeptide by means of a tag-specific purification method; and
 d) removing the tag sequence and the additional amino acid(s) from the elongated (poly)peptide by means of a cleavage method specific for the additional amino acid(s) to obtain the purified polypeptide.

The specific cleavage method is preferably a chemical cleavage method as will be further elucidated hereinbelow.

DETAILED DESCRIPTION OF THE PREFERRED EMBODIMENTS

The method and process of the invention are applicable to every (poly)peptide since they do not depend on the amino acid composition thereof. Furthermore, in certain preferred embodiments the method and process are inexpensive and highly efficient.

Such an embodiment is the use of a methionine residue as the additional amino acid before adding the affinity tag (for example a stretch of six histidine residues or other purification facilitating compounds). After appropriate purification steps, such as tag-specific affinity chromatography, the histidine tag may be cleaved of by CNBr digestion, an inexpensive and very efficient process, which specifically cleaves at the methionine residue.

In a preferred embodiment the tag thus comprises at least a stretch of histidine residues, preferably six or more, and a methionine residue. Optionally one or more other amino acids may be incorporated.

If the sequence of the desired polypeptide contains methionine residues they would be subject to cleavage by cyanogen bromide when removing the tag. However, according to the invention this may be avoided by using modified methionine residues in the synthesis of the (poly) peptide. Such a modified methionine residue is for example methionine sulfoxide.

In an alternative embodiment of the method and process of the invention the tag is a large molecule, such as polyethylene glycol. In this case the tag-specific purification method is gel filtration chromatography.

The method and process of the invention are equally well applicable to polypeptides produced by recombinant DNA techniques. In a preferred embodiment the methionine residues originally present within the desired polypeptide, but not in the tag are cleavage protected, for example by being substituted by another amino acid, such as valine, glycine, or deleted.

In this application "tag" is used to indicate a removable molecule added to the desired polypeptide during or after synthesis thereof. A "tag" may be an amino acid sequence added during synthesis of the polypeptide, but may also be another molecule than can be easily purified out of a mixture of components. An example of the latter is polyethylene glycol (PEG).

In this application the terms "peptide", "polypeptide" and "(poly)peptide" are used interchangeably.

The next example is given for illustrating the invention. It is clear that for the skilled person this example will give enough guidance to develop further methods that fall within the scope of the invention. In the example a purification procedure of general applicability is disclosed, based on the combination of 1) a capping protocol, 2) use of methionine sulfoxide as protected methionine residue during assembly of the native sequence and 3) elongation of the desired peptide with a methionine and 2 glycine residues and a final stretch of 6 histidines which will be used for chromatography affinity. After adequate purification steps, cyanogen bromide cleavage of the histidine tag followed by final reduction of methionine sulfoxide to methionine was performed. This simple, straightforward strategy allowed the purification to homogeneity of the 69 residue polypeptide "PbCS 242-310", covering the C-terminal region of the *Plasmodium berghei* CS protein, in high yield and short time using conventional chromatographic procedures.

EXAMPLE

1. Materials and Methods

1:1. Reagents and Solvents

Chemicals and solvents used for the peptide synthesis were purchased from Calbiochem-Novabiochem AG (L äufelfingen, Switzerland) and Fluka (Buchs, Switzerland).

1.2. Peptide Synthesis and Analysis

To illustrate the present invention a polypeptide designated "PbCS 242-310" covering the C-terminal region of *Plasmodium berghei* CS protein[12] was chemically synthesized using solid phase F-Moc chemistry in an Applied Biosystems 431A Peptide Synthesiser. The polypeptide was prepared on a F-moc-Ser(t-butyl)-p-alkoxybenzylalkohol resin (Wang resin) with a degree of substitution of 0.43 mmol/g at the 0.1 mmol scale. The synthesis was performed using a five fold excess of F-moc amino acid derivatives, DCCI and HOBt as activating agents, a 60 min coupling time for the first 34 amino acids and a double coupling for the following residues. Capping with acetic anhydride was performed at the end of each cycle. Side chain protecting groups included: pentamethylchroman sulfonyl group for Arg; -S-t-butyl for Cys; triphenylmethyl group for Asn, Gln and His; t-butoxycarbonyl group for Lys and Trp; t-butyl group for Asp, Clu, Ser, Thr and Tyr. Met 306 was inserted as Fmoc-Met-sulfoxide to protect it against later cyanogen bromide cleavage.

The peptide was then elongated N-terminally with the sequence His-His-His-His-His-His-Gly-Gly-Met (SEQ ID NO: 1) using the same conditions described above but capping was omitted after coupling of the second Gly. The polypeptide thus obtained is designated "His tag PbCS 242-310".

Crude peptide was obtained by treating the peptide-resin with 2.5% $H_2O$, 5% triethylsilan in TFA for 2 hours at room temperature. Synthetic peptide was purified by size exclusion liquid chromatography (Sephadex G50 column 70×2.5 cm using 50% acetic acid/$H_2O$ as mobile phase). The purity of peptide was analyzed by RP-HPLC using a C4 W-Porex 250×4.6 mm column and a 10–90% $CH_3CN$ gradient in 0.1% TFA/$H_2O$ in 60 min with a flow rate of 1.0 ml/min. The amino acid composition was determined according to Knecht and Chang[13].

1.3. Immobilized Metal Ion Affinity Chromatography (IMAC) and CNBr Cleavage

The polypeptide was first purified by affinity chromatography based on the histidine tag. Afterwards the tag was removed by cyanogen bromide.

A Ni-column was prepared with Ni-NTA agarose resin (Qiagen Inc., Chatsworth, USA) and equilibrated with buffer A (8M urea, 0.1 M $Na_2HPO_4$, 0.01 M Tris, pH adjusted to 8.0 with $H_3PO_4$). Size exclusion purified "His-tag PbCS 242-310" polypeptide was dissolved in Buffer A and loaded on the column with a flow rate of 15 ml/h. The column was washed with buffer A (flow rate 15 ml/h) and buffer B (8M urea, 0.1 M $Na_2HPO_4$, 0.01 M Tris, pH adjusted to 6.3 with $H_3PO_4$) containing 50 mM imidazole at a flow rate of 30 ml/h. The "His-tag PbCS 242-310" polypeptide was then eluted (flow rate 30 ml/h) with buffer B containing 250 mM imidazole.

The eluted material was desalted by a Sephadex G25 column (50×2.5 cm using 50% acetic acid/$H_2O$ as mobile phase) and lyophilized. For removal of the histidine tag the thus obtained material was treated for 8 hours at RT at a concentration of 20 mg/ml in 70% TFA using a 100 fold molar excess of CNBr.

The thus digested material was lyophilized, solubilized in Buffer A and loaded again on the Ni-NTA agarose column. The histidine tag.is retained on the Ni-column and the flow through of the column contains the "PbCS 242-310" polypeptide. The flow through was desalted by a Sephadex G25 column (50×2.5 cm using 50% acetic acid/H$_2$O as mobile phase) and lyophilized.

1.4. Met-Sulfoxide Reduction

The CnBr treated and IMAC purified material was treated with 10% mercaptoethanol at pH 8.0 to convert methionine sulfoxide into methionine and Cys-S-t-butyl into Cys and then further purified by gel filtration (Sephadex G25 column 250×4.4 mm).

1.5. Mass Spectrometry

Mass Spectrometry analysis was performed using a time-of-flight mass spectrometer LDI 1700 Mass Monitor (Linear Scientific Inc., Reno, N.V., USA). Five μl of a solution of 1 mg/ml of polypeptide were mixed with 5 μl of trans-3,5-dimethoxy-4-hydroxycinnamic acid (sinapinic acid) (20 mg/ml in acetonitrile (Linear Scientific Inc. Reno, N.V., USA)) and 1.0 μl of this solution was placed on the mass spectrometer probe tip and dried with a gently vacuum. The sample was irradiated with 3-ns laser pulses (wavelength 337 nm) from a N$_2$-Laser. Time-of-flight was measured with a digital oscilloscope (series 9304; Le Croy Research Systems, Corp., Spring Valley, N.Y.) which was converted into mass spectrum using the Peptide MALDI-TOFMS Calibration Standard (Linear Scientific Inc., Reno, N.V., USA).

2. Results

The 69 residue polypeptide "PbCS 242-310" corresponds to the C-terminal region of *P. berghei* CS protein[12]. Synthesis of "His-tag PbCS 242-310" was performed using an automatic protocol in which a capping step was included after each coupling as described in the "Materials and Methods" section.

More than 150 mg of crude polypeptide were obtained by treating 600 mg of the corresponding peptide resin with H$_2$O/triethylsilan/TFA.

Figure 1:
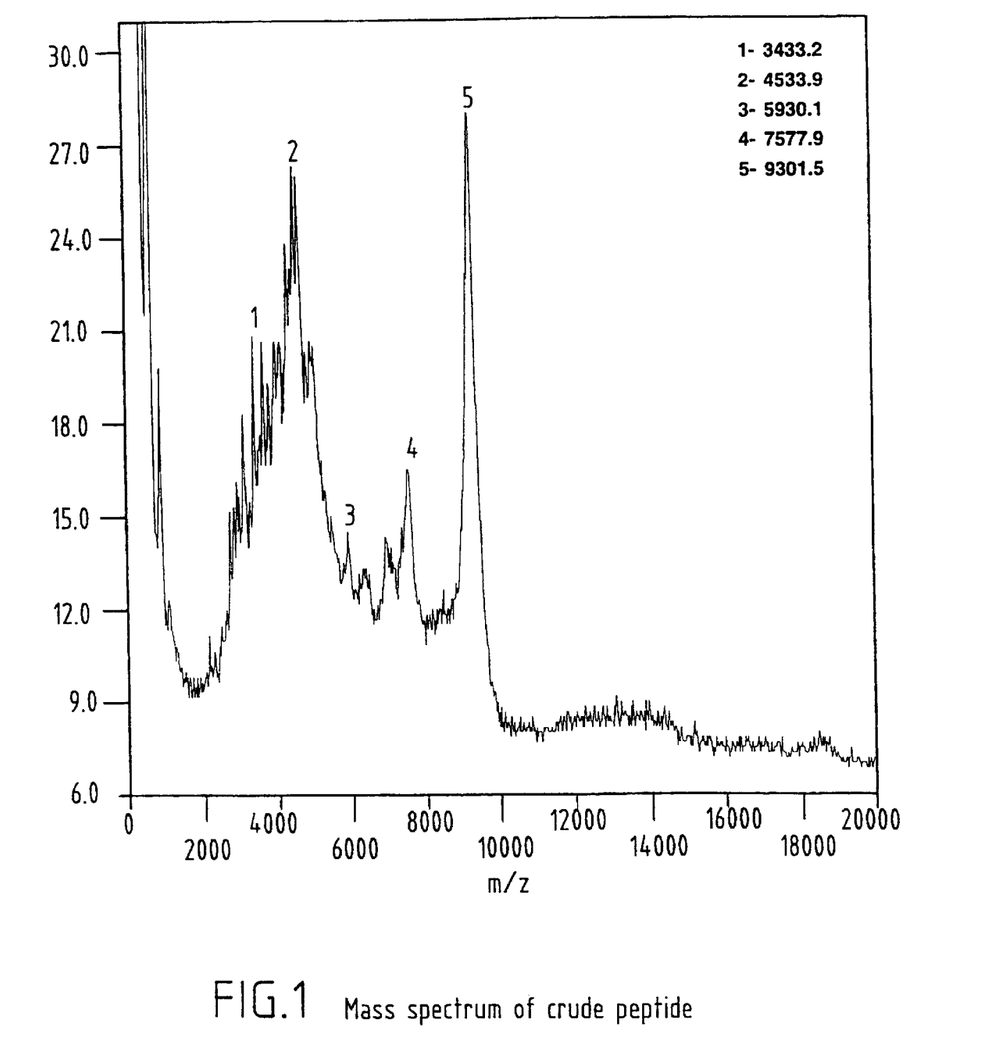
FIG. 1 is a mass spectrum of crude peptide.

Mass spectral analysis of the crude polypeptide indicated the presence of the species of interest with a Molecular Weight (MW) of 9301 among other low MW components (FIG. 1).

Figure 2:
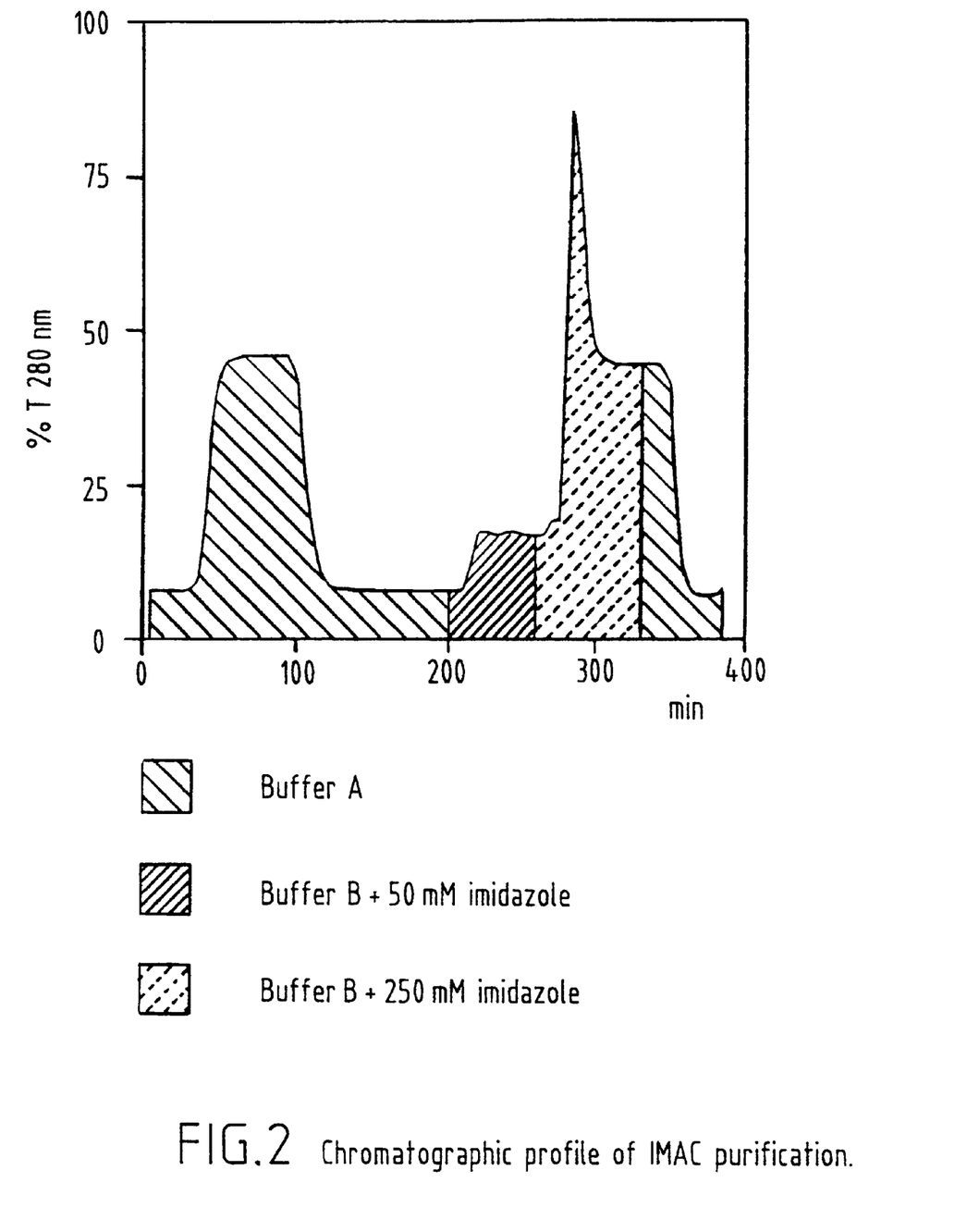
FIG. 2 is a chromatographic profile of IMAC purification.

Ninety mg of crude polypeptide were purified by immobilized metal ion affinity chromatography (IMAC) on a 25 ml volume Ni-NTA agarose column (FIG. 2). After desalting by size exclusion liquid chromatography 35 mg of "His-tag PbCS 242-310" were obtained. The measurement of the absorbance at 280 nm of the eluted material (35 mg) and of the flow through (55 mg) indicated that the yield of the purification protocol was 100%.

The Ni-column purified material was then cleaved with CNBr to eliminate the 6xHis tag.

The digested material was reloaded on the Ni-column to eliminate the uncleaved peptide and treated with 10% mercaptoethanol at pH 8.0 in order to reduce the methionine sulfoxide inserted during the synthesis and the Cys residue protective groups. The complete reduction of the methionine sulfoxide was confirmed by retreating the material with CNBr and checking the efficacy of the cleavage by mass spectrometry.

Further purification by size exclusion chromatography resulted in 19 mg of purified PbCS 242-310.

Figure 3:
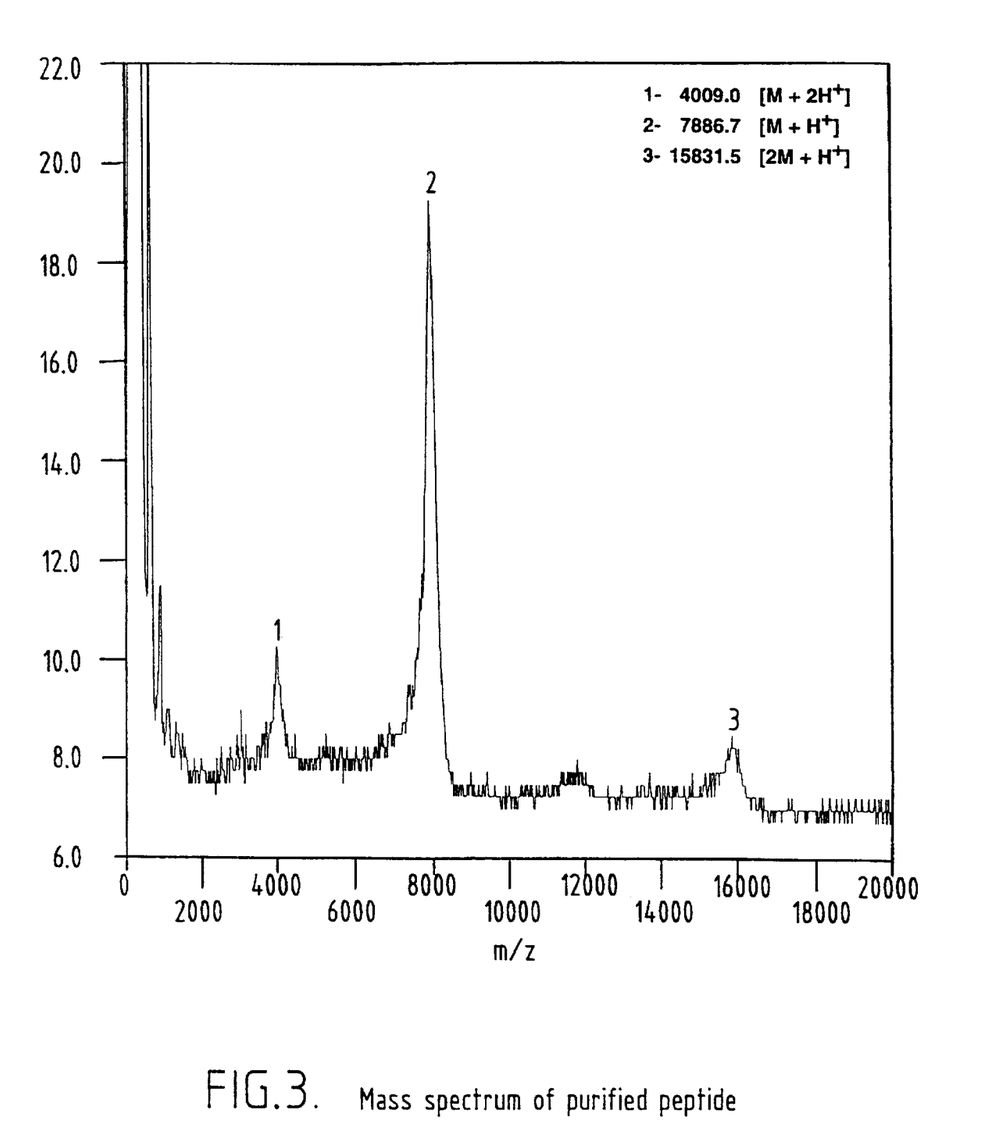
FIG. 3 is a mass spectrum of purified peptide.
Figure 4:
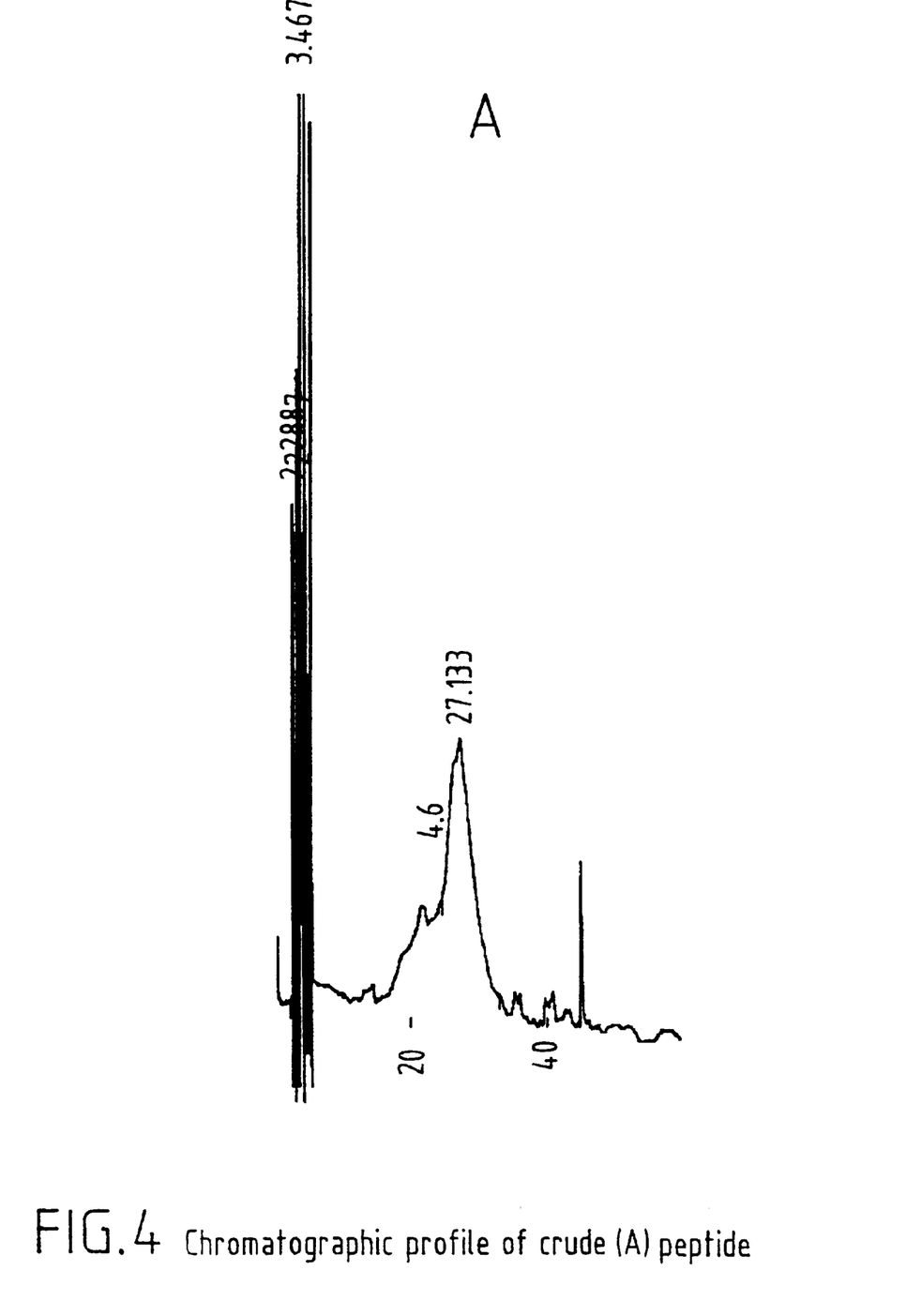
FIGS. 4A and 4B are chromatographic profiles of crude and purified peptide.

In FIG. 3 the mass spectrum of the obtained material is shown and in FIG. 4 the analytical chromatographic profiles of crude and purified peptide are compared. The difference of retention times between the two runs is due to the absence of the highly charged His tag in the purified material. The purified "PbCS 242-310" was found to be about 95% pure based on the integration of peak areas when analyzed at 214 nm. The amino acid composition of the CS polypeptide was consistent with that expected for this peptide (Table 1).

TABLE 1

Amino acid analysis

| | Residues per mole of PbCS 242-310 | | |
|---|---|---|---|
| Amino acid[a] | Expected | Observed[b] | S.D.[c] |
| Asp + Asn | 10 | 9.4 | 1.0 |
| Glu + Gln | 9 | 9.1 | 0.9 |
| Ser | 7 | 8.4 | 2.1 |
| Thr | 4 | 2.2 | 0.8 |
| Gly | 3 | 3.1 | 1.0 |
| Ala | 2 | 3.4 | 1.1 |
| Arg | 4 | 4.8 | 0.9 |
| Pro | 1 | 1.1 | 0.2 |
| Val | 3 | 2.9 | 0.3 |
| Met | 1 | 1.0 | 0.1 |
| Ile | 7 | 6.3 | 0.7 |
| Leu | 3 | 3.3 | 0.2 |
| Phe | 1 | 1.1 | 0.1 |
| Lys | 8 | 6.7 | 1.0 |
| His | 0 | — | — |
| Tyr | 1 | 1.2 | 0.2 |

[a]Both Cys and Trp are not determinated
[b]Mean value of five determination
[c]Standard deviation 3. Discussion Chemical synthesis of bioactive peptides has become a widespread and rapidly growing technique due to the automation and efficient protocols for chain assembly. For most applications, the crude synthetic product must be purified to remove residuals reactants, failure sequences and chemically modified peptide species. This is usually accomplished by reversed-phase HPLC using aqueous trifluoroacetic acid/acetonitrile mobile phases. Although peptide synthesis has become highly automated, purification is still largely a manual process and therefore time-consuming, expensive and not very efficient.

This example has shown that the process of the invention leads to high purity as follows from FIG. 3 and is easy to perform and universally applicable.

The problem of a specific cleavage due to the presence of Met residues in the desired sequence, as in the case described herein, is according to the invention easily circumvented using Met-sulfoxide residues which are resistant to CNBr treatment and quantitatively reducible with mercaptoacetic acid[14].

From the above it follows that the process of the invention was successfully applied for the purification of the polypeptide "PbCS 242-310", a 69 residue chain corresponding to C-terminal region of *P. berghei* CS protein[12]. Although many peptide impurities were present in the crude material after cleavage from the resin as shown by mass spectral analysis reported in FIG. 1, the inventors were able to purify the target peptide to homogeneity in high yield and in relatively short time. The complete protocol of purification yielded 19 mg of purified PbCS 242-310, corresponding to about 20% of the crude material.

In conclusion, it was demonstrated here that CNBr cleavage and protection of relevant Met residues as sulfoxides, coupled with an efficient affinity tag can represent an efficient and general tool for the purification of chemically synthesized long chain peptides.

REFERENCES

1. Chong, P., Sia, C., Tam, E., Kandil, A. & Klein, M. International Journal of Peptide & Protein Research 41, 21–27 (1993).
2. Haaheim, L. R., Maskell, J. P., Mascagni, P. & Coates, A. R. Scandinavian Journal of Immunology 34, 341–350 (1991).
3. Roggero, M. A., et al. Molecular Immunology 32, 1301–1309 (1995).
4. Smith, D. D., et al. International Journal of Peptide & Protein Research 44, 183–191 (1994).
5. Lobl, T. J., Deibel, M. J. & Yem, A. W. Analytical Biochemistry 170, 502–511 (1988).
6. Tomasselli, A. G., et al. Journal of Biological Chemistry 267, 10232–10237 (1992).
7. Ball, H. L. & Mascagni, P. International Journal of Peptide & Protein Research 40, 370–379 (1992).
8. Krieger, D. E., Erickson, B. W. & Merrifield, R. B. Proceedings of the National Academy of Sciences of the United States of America 73, 3160–3164 (1976).
9. Lindeberg, G., Tengborn, J., Bennich, H. & Ragnarsson, U. J. Chromatography 156, 366–369 (1978).
10. Porath, J., Carlsson, J., Olsson, I. & Belfrage, G. Nature 258, 598–599 (1975).
11. Lindeberg, G., Bennich, H. & Engstrom, A. International Journal of Peptide & Protein Research 38, 253–259 (1991).
12. Lanar, D. E. Mol. Biochem Parasitol. 39, 151–154 (1990).
13. Knecht, R. & Chang, J. Y. Analyt. Chem. 58, 2375–2379 (1986).
14. Houghten, R. A. & Li, C. H. Methods in enzymology 91, 549–559 (1991).
15. Barany, G. & Merrifield, R. B. Peptides, analysis, synthesis, biology 1-163–165 (Academic Press, London, 1980).

synthesis thereof and protecting methionine residues within the (poly)peptide, if present, against cleavage, by protecting them with a sulfoxide group, wherein the tag is one of a his tag and a large molecule.

2. A process for the preparation of purified (poly)peptides using the modification method of claim 1, comprising the steps of:
   a) synthesizing the desired (poly)peptide;
   b) adding at least one specifically cleavable methionine at the end of the (poly)peptide, while having protected methionine(s) within the (poly)peptide, if present, against cleavage by protection with a sulfoxide group;
   c) elongating the (poly)peptide and the methionine(s) added thereto with a tag to obtain an elongated (poly)peptide;
   d) purifying the elongated (poly)peptide by means of a tag-specific purification method; and
   e) removing the tag and the additional methionine(s) from the elongated (poly)peptide by means of a cleavage method based on cyanogen bromide to obtain purified (poly)peptide, wherein the tag is one of a his tag sequence and a large molecule.

3. The process as claimed in claim 2, wherein the his tag sequence consists of His-His-His-His-His-His-Gly-Gly- (SEQ ID NO: 1).

4. The process as claimed in claim 2, wherein the tag-specific purification method is chromatography based on affinity for the tag sequence.

5. The process as claimed in claim 2, wherein the tag is a large molecule and the tag-specific purification method is gel filtration chromatography.

6. The process as claimed in claim 2, wherein the desired (poly)peptide is produced by recombinant DNA techniques in a living host and further comprising the step of deleting

What is claimed is:

1. A method for the modification of (poly)peptides for facilitating purification thereof, comprising the steps of:

inserting at least one specifically cleavable methionine and a tag at the end of a (poly)peptide chain during or substituting with another amino acid any methionines within the (poly)peptide.

7. The process as claimed in claim 6, wherein the living host is one of a eukaryotic host and a prokaryotic host.

8. The process as claimed in claim 5, wherein the tag is polyethylene glycol.

* * * * *

UNITED STATES PATENT AND TRADEMARK OFFICE
CERTIFICATE OF CORRECTION

PATENT NO.     : 6,075,127                                    Page 1 of 1
DATED          : June 13, 2000
INVENTOR(S)    : Mario Roggero et al.

It is certified that error appears in the above-identified patent and that said Letters Patent is hereby corrected as shown below:

<u>Title page,</u>
Under [56] References Cited, insert :
-- U.S. PATENT DOCUMENTS
5,391,711  3/1995        Funakoshi et al..........530/344
          FOREIGN PATENT DOCUMENTS
0329662  8/1989        EPO
          OTHER PUBLICATIONS
Ball et al., "purification of synthetic Peptides Using Reversible Chromatographic Porbes Based on the FMOC Molecule, "Int. J. Pept. Prot. Res. 40(5): 370-379.

Lindeberg et al., "Purification of Synthetic Peptides Immobilized Metal Ion Affinity Chromatography (IMAC)", Int. J. Pept. Prot. Res. 38(3): 253-259. --

Signed and Sealed this

Fourteenth Day of August, 2001

*Attest:*

NICHOLAS P. GODICI
*Attesting Officer*     *Acting Director of the United States Patent and Trademark Office*